United States Patent
Retsina et al.

(10) Patent No.: US 12,291,731 B2
(45) Date of Patent: May 6, 2025

(54) METHODS AND SYSTEMS FOR ENZYMATIC HYDROLYSIS OF PRETREATED BIOMASS AT HIGH SOLIDS CONCENTRATIONS

(71) Applicant: GranBio Intellectual Property Holdings, LLC, Minnetrista, MN (US)

(72) Inventors: Theodora Retsina, Atlanta, GA (US); Ryan Zebroski, Fayetteville, GA (US)

(73) Assignee: GranBio Intellectual Property Holdings, LLC, Thomaston, GA (US)

( * ) Notice: Subject to any disclaimer, the term of this patent is extended or adjusted under 35 U.S.C. 154(b) by 0 days.

(21) Appl. No.: 17/568,802

(22) Filed: Jan. 5, 2022

(65) Prior Publication Data

US 2022/0205005 A1 Jun. 30, 2022

Related U.S. Application Data

(63) Continuation of application No. 16/029,929, filed on Jul. 9, 2018, now abandoned, which is a continuation of application No. 15/276,834, filed on Sep. 27, 2016, now abandoned.

(60) Provisional application No. 62/234,415, filed on Sep. 29, 2015.

(51) Int. Cl.
*C12P 19/02* (2006.01)
*C12P 19/14* (2006.01)

(52) U.S. Cl.
CPC ............... *C12P 19/02* (2013.01); *C12P 19/14* (2013.01); *C12P 2203/00* (2013.01)

(58) Field of Classification Search
CPC ........ C12P 19/02; C12P 19/14; C12P 2203/00
See application file for complete search history.

(56) References Cited

U.S. PATENT DOCUMENTS

2008/0057555 A1* 3/2008 Nguyen ................... C12P 7/10
435/165

OTHER PUBLICATIONS

Qing et al. Impact of surfactants on pretreatment of corn stover, Bioresource Technology 101 (2010) 5941-5951. (Year: 2010).*
Xiao et al. Effects of sugar inhibition on cellulases and beta-glucosidase enzyme activity during enzymatic hydrolysis of softwood substrates, Applied Biochemistry and Biotechnology, (2004), vol. 113-116, p. 1115-1126. (Year: 2004).*
Wang et al. Lignosulfonate-mediated cellulase adsorption: enhanced enzymatic saccharification of lignocellulose through weakening nonproductive binding to lignin. Biotechnology for Biofuels (2013), 6:156, p. 1-10). (Year: 2013).*

* cited by examiner

*Primary Examiner* — Iqbal H Chowdhury
(74) *Attorney, Agent, or Firm* — O'Connor & Company; Ryan P. O'Connor

(57) ABSTRACT

A method of enzymatically hydrolyzing pretreated lignocellulosic biomass at high solids concentration includes introducing pretreated biomass to a hydrolysis reactor, to hydrolyze the cellulose to glucose monomer and glucose oligomers, and circulating a liquid stream, from which glucose is removed to reduce glucose inhibition of cellulose hydrolysis. A surfactant may be added to the hydrolysis reactor. Heat and/or acid treatment of the glucose oligomers may be used to generate additional glucose monomer. Some variations introduce pretreated biomass to a hydrolysis reactor to hydrolyze cellulose to glucose monomer and glucose oligomers, followed by conveying a portion of the solid phase to a mechanical refiner and/or a unit under reduced pressure, to generate a refined and/or exploded solid phase; and recycling the refined and/or exploded solid phase, optionally reheated, back to an input of the hydrolysis reactor.

4 Claims, 3 Drawing Sheets

METHODS AND SYSTEMS FOR ENZYMATIC HYDROLYSIS OF PRETREATED BIOMASS AT HIGH SOLIDS CONCENTRATIONS

PRIORITY DATA

This application is a continuation application of U.S. patent application Ser. No. 16/029,929, filed on Jul. 9, 2018, which is a continuation application of U.S. patent application Ser. No. 15/276,834, filed on Sep. 27, 2016, which claims priority to U.S. Provisional Patent App. No. 62/234,415, filed on Sep. 29, 2016, each of which is incorporated by reference herein.

FIELD OF THE INVENTION

The present invention generally relates to methods and systems for preparing fermentable sugars from lignocellulosic biomass.

BACKGROUND OF THE INVENTION

Enzymatic hydrolysis is a key process for a biorefinery based on production of sugars. The rate of enzymatic hydrolysis, final carbohydrate conversion, and concentration all critically affect the technoeconomic feasibility of commercial operations. Enzymatic hydrolysis performed at high solids loading offers several advantages over low solids loading, because of higher sugar and bioproduct concentrations, smaller equipment, less energy for heating and cooling of the slurry, and lower hydraulic loads. Therefore, enzymatic hydrolysis at high solids loadings is highly desirable to develop an economically viable process. See Geng et al., "Strategies to achieve high-solids enzymatic hydrolysis of dilute-acid pretreated corn stover," *Bioresource Technology* 187 (2015) 43-48.

However, hydrolysis at high insoluble solids introduces a lack of available water in the reactor. Water is essential to the hydrolysis and conversion of lignocellulosic biomass since it is the key medium for enzymes to diffuse in and for products to diffuse away from reaction sites. Water also reduces the viscosity of the slurry by increasing the lubricity of the particles, which decreases the required shear stress necessary to produce a given shear rate, allowing lower power input for mixing during hydrolysis. Therefore, high-solids hydrolysis can create rheological challenges, cause insufficient mixing, reduce mass- and heat-transfer efficiency, and increase the concentration of enzymes inhibitors in the system, resulting in low conversion of carbohydrates into fermentable sugars.

To overcome the challenges of enzymatic hydrolysis at high solids and make the overall conversion process more economically viable, several approaches have been developed, including fed-batch, splitting/thickening, and clarifier processes.

For the fed-batch process, substrates and/or enzymes are introduced into a hydrolysis reactor successively. The fed-batch system allows time for the slurry to liquefy before adding additional solids and a low initial insoluble solids content can be kept. In order to maintain high rates of carbohydrate conversion of hydrolysis, it is important to find an optimal point to add solids into the system, which is highly dependent on substrate characteristics and enzyme dosage/type.

For the splitting/thickening process, pretreated substrate is mixed with part of the enzymes at a lower solids loading and then filtered to obtain the desired solids loading. Using split addition, the solids content can be increased to 20% while maintaining the enzymatic hydrolysis conversion efficiency comparable to that with 5% total solids.

For the clarifier process, a gravity clarifier separates the partially hydrolyzed stream into a sugar stream and unhydrolyzed solids, and the sugar stream is used to dilute the initial insoluble solids content. This process can reduce the initial viscosity without decreasing the final sugar concentration because of the high sugar concentration of the sugar stream.

Improvements are still desired to reach high solids concentrations in enzymatic hydrolysis of pretreated biomass.

SUMMARY OF THE INVENTION

The present invention addresses the aforementioned needs in the art.

Some variations provide a method of enzymatically hydrolyzing pretreated lignocellulosic biomass at high solids concentration, the method comprising:
(a) providing pretreated lignocellulosic biomass containing cellulose;
(b) introducing the pretreated lignocellulosic biomass to a hydrolysis reactor under effective hydrolysis conditions and in the presence of enzymes including cellulases, to hydrolyze the cellulose to glucose monomer and glucose oligomers; and
(c) circulating a liquid stream in a circulation line configured from an output of the reactor back to an input of the hydrolysis reactor, wherein at least a portion of the glucose is removed from the circulation line to reduce glucose inhibition of cellulose hydrolysis.

In some embodiments, the method further comprises introducing a surfactant to the hydrolysis reactor during step (b) or step (c). The surfactant may include lignin, such as hardwood lignin, for example.

In some embodiments, the method further comprises an oligomer hydrolysis step comprising heat treatment and/or acid treatment of the glucose oligomers to generate additional glucose monomer. The oligomer hydrolysis step may be integrated with step (b) and/or step (c). Additional enzymes may be introduced to the circulation line or at another location.

Optionally, at least a portion of the glucose oligomers may be removed from the circulation line to reduce glucose oligomer inhibition of cellulose hydrolysis. The removal of glucose oligomers may target cellobiose, which is a relatively high enzyme inhibition effect, compared to larger oligomers.

Some variations provide a method of enzymatically hydrolyzing pretreated lignocellulosic biomass at high solids concentration, the method comprising:
(a) providing pretreated lignocellulosic biomass containing cellulose;
(b) introducing the pretreated lignocellulosic biomass to a hydrolysis reactor under effective hydrolysis conditions and in the presence of enzymes including cellulases, to hydrolyze a portion of the cellulose to glucose monomer and glucose oligomers present in a liquid phase, wherein non-hydrolyzed cellulose remains in a solid phase; and
(c) conveying a portion of the solid phase to a mechanical refiner, to generate a refined solid phase; and
(d) recycling the refined solid phase back to an input of the hydrolysis reactor.

Some variations provide a method of enzymatically hydrolyzing pretreated lignocellulosic biomass at high solids concentration, the method comprising:

(a) providing pretreated lignocellulosic biomass containing cellulose;
(b) introducing the pretreated lignocellulosic biomass to a hydrolysis reactor under effective hydrolysis conditions and in the presence of enzymes including cellulases, to hydrolyze a portion of the cellulose to glucose monomer and glucose oligomers present in a liquid phase, wherein non-hydrolyzed cellulose remains in a solid phase;
(c) feeding a portion of the solid phase to a unit under reduced pressure, to generate an exploded solid phase; and
(d) recycling the exploded solid phase, optionally reheated, back to an input of the hydrolysis reactor.

Some variations provide a method of enzymatically hydrolyzing pretreated lignocellulosic biomass at high solids concentration, the method comprising:

(a) providing pretreated lignocellulosic biomass containing cellulose;
(b) introducing the pretreated lignocellulosic biomass to a hydrolysis reactor under effective hydrolysis conditions and in the presence of enzymes including cellulases, to hydrolyze a portion of the cellulose to glucose monomer and glucose oligomers present in a liquid phase, wherein non-hydrolyzed cellulose remains in a solid phase;
(c) conveying a portion of the solid phase to a mechanical refiner, to generate a refined solid phase;
(d) feeding the refined solid phase to a unit under reduced pressure, to generate an exploded and refined solid phase; and
(e) recycling the exploded and refined solid phase, optionally reheated, back to an input of the hydrolysis reactor.

In some embodiments, the method further comprises introducing a surfactant to the hydrolysis reactor. In some embodiments, the method further comprises an oligomer hydrolysis step comprising heat treatment and/or acid treatment of the glucose oligomers to generate additional glucose monomer.

In various embodiments, the pretreated lignocellulosic biomass is chemically pretreated (e.g., with an acid or base), physically pretreated (e.g., refined or exploded), or a combination thereof. The pretreated lignocellulosic biomass may be a pulp material, derived from wood or lignocellulosic biomass, selected from the group consisting of kraft pulp, sulfite pulp, soda pulp, mechanical pulp, thermomechanical pulp, chemimechanical pulp, and combinations thereof.

In certain embodiments, the pretreated lignocellulosic biomass is GP3+® pulp derived from wood or lignocellulosic biomass. The pretreated lignocellulosic biomass may be obtained from steam or hot-water extraction of lignocellulosic biomass.

In certain embodiments, the pretreated lignocellulosic biomass is AVAP® pulp derived from wood or lignocellulosic biomass. The pretreated lignocellulosic biomass may be obtained from fractionation of lignocellulosic biomass in the presence of water, an acid catalyst, and a solvent for lignin.

In preferred embodiments, the pretreated lignocellulosic biomass is present in the hydrolysis reactor at a solids concentration of about 15 wt % or more, about 20 wt % or more, about 25 wt % or more, or about 30 wt % or more.

Enzymes may be introduced to the pretreated lignocellulosic biomass at multiple times and/or locations. The concept of split addition of enzymes may be applied. In some embodiments, a first amount of enzymes is introduced at a first solids concentration, a second amount of enzymes is introduced at a second solids concentration, the second solids concentration being higher than the first solids concentration.

Also provided is a system configured for carrying out a method as described.

Also provided is a sugar product produced by a process comprising a method as described. A fermentation product (e.g., ethanol) may be derived from the sugar product.

DETAILED DESCRIPTION OF EMBODIMENTS OF THE INVENTION

Figure 1:
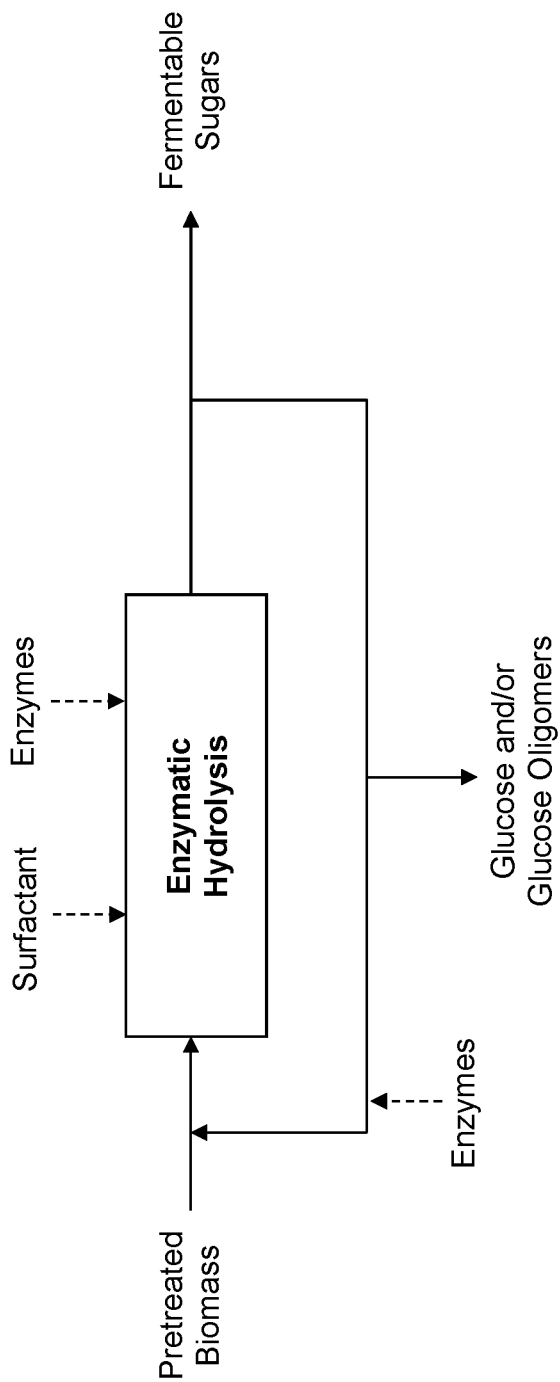
FIG. 1 is a simplified block-flow diagram depicting the process of some embodiments of the present invention.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Some variations provide a method of enzymatically hydrolyzing pretreated lignocellulosic biomass at high solids concentration, the method comprising:
(a) providing pretreated lignocellulosic biomass containing cellulose;
(b) introducing the pretreated lignocellulosic biomass to a hydrolysis reactor under effective hydrolysis conditions and in the presence of enzymes including cellulases, to hydrolyze the cellulose to glucose monomer and glucose oligomers; and
(c) circulating a liquid stream in a circulation line configured from an output of the reactor back to an input of the hydrolysis reactor, wherein at least a portion of the glucose is removed from the circulation line to reduce glucose inhibition of cellulose hydrolysis.

For example, see FIG. 1 for an illustration of some embodiments.

In some embodiments, the method further comprises introducing a surfactant to the hydrolysis reactor during step (b) or step (c). The surfactant may include lignin, such as hardwood lignin, for example.

In some embodiments, the method further comprises an oligomer hydrolysis step comprising heat treatment and/or acid treatment of the glucose oligomers to generate additional glucose monomer. The oligomer hydrolysis step may be integrated with step (b) and/or step (c). Additional enzymes may be introduced to the circulation line or at another location.

Optionally, at least a portion of the glucose oligomers may be removed from the circulation line to reduce glucose oligomer inhibition of cellulose hydrolysis. The removal of glucose oligomers may target cellobiose, which is a relatively high enzyme inhibition effect, compared to larger oligomers.

Some variations provide a method of enzymatically hydrolyzing pretreated lignocellulosic biomass at high solids concentration, the method comprising:
(a) providing pretreated lignocellulosic biomass containing cellulose;
(b) introducing the pretreated lignocellulosic biomass to a hydrolysis reactor under effective hydrolysis conditions and in the presence of enzymes including cellulases, to hydrolyze a portion of the cellulose to glucose monomer and glucose oligomers present in a liquid phase, wherein non-hydrolyzed cellulose remains in a solid phase; and
(c) conveying a portion of the solid phase to a mechanical refiner, to generate a refined solid phase; and
(d) recycling the refined solid phase back to an input of the hydrolysis reactor.

Figure 2:
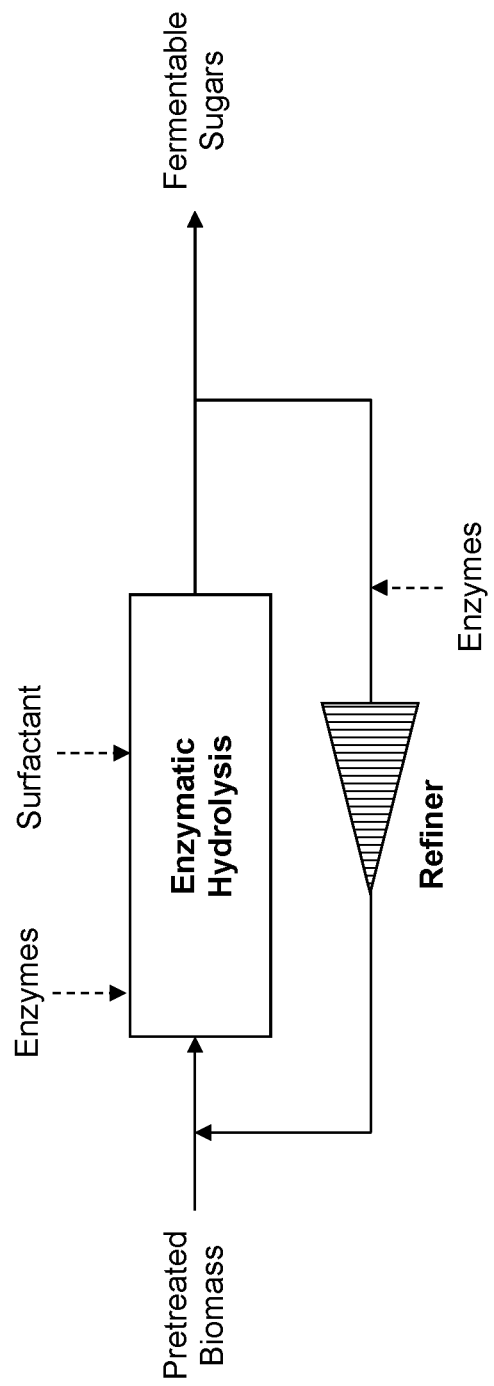
FIG. 2 is a simplified block-flow diagram depicting the process of some embodiments of the present invention.

For example, see FIG. 2 for an illustration of some embodiments.

The mechanical refiner can be configured to cause cellulose chain end-opening action, for enhanced enzyme accessibility.

Some variations provide a method of enzymatically hydrolyzing pretreated lignocellulosic biomass at high solids concentration, the method comprising:
(a) providing pretreated lignocellulosic biomass containing cellulose;
(b) introducing the pretreated lignocellulosic biomass to a hydrolysis reactor under effective hydrolysis conditions and in the presence of enzymes including cellulases, to hydrolyze a portion of the cellulose to glucose monomer and glucose oligomers present in a liquid phase, wherein non-hydrolyzed cellulose remains in a solid phase;
(c) feeding a portion of the solid phase to a unit under reduced pressure, to generate an exploded solid phase; and
(d) recycling the exploded solid phase, optionally reheated, back to an input of the hydrolysis reactor.

Figure 3:
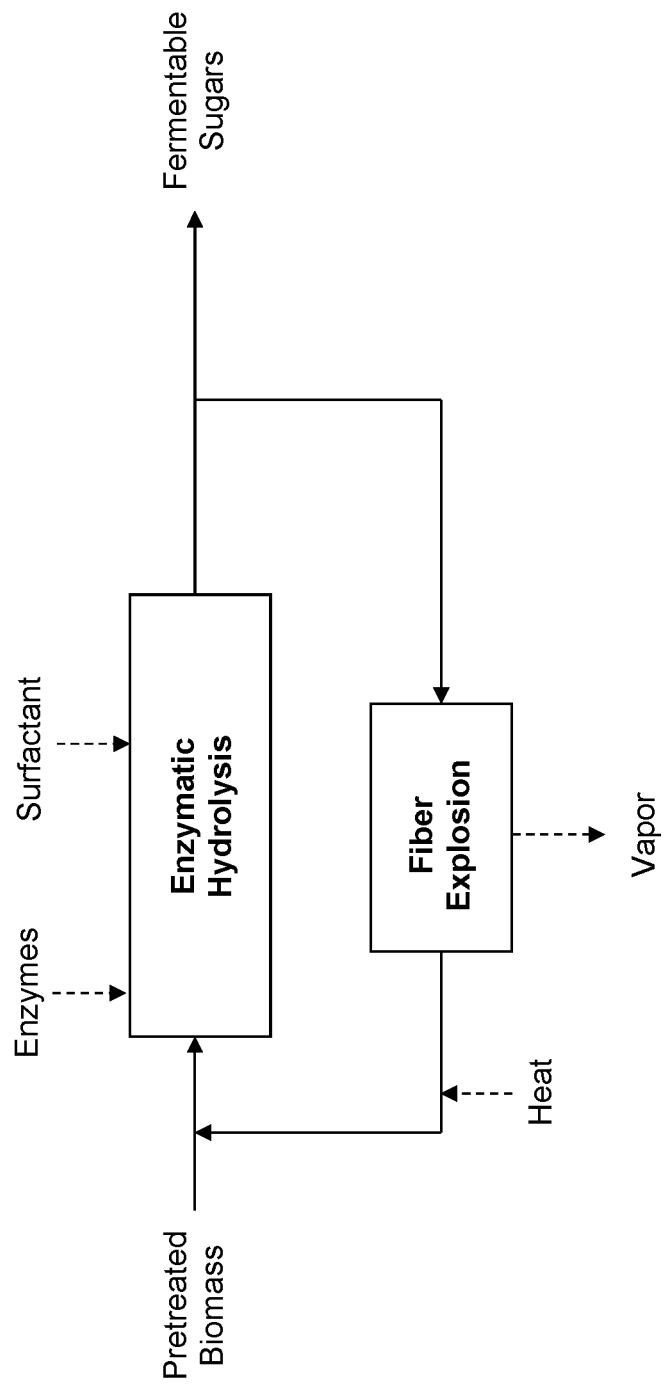
FIG. 3 is a simplified block-flow diagram depicting the process of some embodiments of the present invention.

For example, see FIG. 3 for an illustration of some embodiments.

The unit under reduced pressure (e.g., vacuum) can be configured to cause cellulose fiber expansion, for enhanced enzyme accessibility.

Some variations provide a method of enzymatically hydrolyzing pretreated lignocellulosic biomass at high solids concentration, the method comprising:
(a) providing pretreated lignocellulosic biomass containing cellulose;
(b) introducing the pretreated lignocellulosic biomass to a hydrolysis reactor under effective hydrolysis conditions and in the presence of enzymes including cellulases, to hydrolyze a portion of the cellulose to glucose monomer and glucose oligomers present in a liquid phase, wherein non-hydrolyzed cellulose remains in a solid phase;
(c) conveying a portion of the solid phase to a mechanical refiner, to generate a refined solid phase;
(d) feeding the refined solid phase to a unit under reduced pressure, to generate an exploded and refined solid phase; and
(e) recycling the exploded and refined solid phase, optionally reheated, back to an input of the hydrolysis reactor.

In some embodiments, the method further comprises introducing a surfactant to the hydrolysis reactor. In some embodiments, the method further comprises an oligomer hydrolysis step comprising heat treatment and/or acid treatment of the glucose oligomers to generate additional glucose monomer.

In various embodiments, the pretreated lignocellulosic biomass is chemically pretreated (e.g., with an acid or base), physically pretreated (e.g., refined or exploded), or a combination thereof. The pretreated lignocellulosic biomass may be a pulp material, derived from wood or lignocellulosic biomass, selected from the group consisting of kraft pulp, sulfite pulp, soda pulp, mechanical pulp, thermomechanical pulp, chemimechanical pulp, and combinations thereof.

In certain embodiments, the pretreated lignocellulosic biomass is GP3+® pulp derived from wood or lignocellulosic biomass. The pretreated lignocellulosic biomass may be obtained from steam or hot-water extraction of lignocellulosic biomass.

In certain embodiments, the pretreated lignocellulosic biomass is AVAP® pulp derived from wood or lignocellulosic biomass. The pretreated lignocellulosic biomass may be obtained from fractionation of lignocellulosic biomass in the presence of water, an acid catalyst, and a solvent for lignin.

In preferred embodiments, the pretreated lignocellulosic biomass is present in the hydrolysis reactor at a solids concentration of about 15 wt % or more, about 20 wt % or more, about 25 wt % or more, or about 30 wt % or more.

Enzymes may be introduced to the pretreated lignocellulosic biomass at multiple times and/or locations. The concept of split addition of enzymes may be applied. In some embodiments, a first amount of enzymes is introduced at a first solids concentration, a second amount of enzymes is introduced at a second solids concentration, the second solids concentration being higher than the first solids concentration.

Also provided is a system configured for carrying out a method as described.

Also provided is a sugar product produced by a process comprising a method as described. A fermentation product (e.g., ethanol) may be derived from the sugar product.

Some variations are premised on the discovery of a surprisingly simple process for converting lignocellulosic biomass into fermentable sugars. Biomass may be subjected to a steam or hot-water soak to dissolved hemicelluloses, with or without acetic acid recycle. This step is followed by mechanical refining, such as in a hot-blow refiner, of the cellulose-rich (and lignin-rich) solids. The refined solids are then enzymatically hydrolyzed to generate sugars. A stripping step for removing fermentation inhibitors in the hydrolysate may be included.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

Some variations provide a process for producing fermentable sugars from cellulosic biomass, the process comprising:
(a) providing a feedstock comprising cellulosic biomass;
(b) digesting the feedstock with a reaction solution including steam and/or hot water in a digestor under effective reaction conditions to produce a digested stream containing cellulose-rich solids, hemicellulose oligomers, and lignin;
(c) conveying the digested stream through a mechanical refiner, thereby generating a refined stream with reduced average particle size of the cellulose-rich solids;
(d) separating a vapor from the refined stream;
(e) introducing the refined stream to an enzymatic hydrolysis unit under effective hydrolysis conditions to produce sugars from the cellulose-rich solids and optionally from the hemicellulose oligomers; and
(f) recovering or further processing at least some of the sugars as fermentable sugars.

In some embodiments, the reaction solution comprises steam in saturated, superheated, or supersaturated form. In some embodiments, the reaction solution comprises pressurized hot water.

In some embodiments, the reaction solution further comprises an acid, such as a sulfur-containing acid (e.g., sulfuric acid, sulfurous acid, or sulfur dioxide), acetic acid, formic acid, or others. The acid may include acetic acid recovered from the digested stream.

The mechanical refiner may be selected from the group consisting of a hot-blow refiner, a hot-stock refiner, a blow-line refiner, a disk refiner, a conical refiner, a cylindrical refiner, an in-line defibrator, a homogenizer, and combinations thereof. In some embodiments, the mechanical refiner is a blow-line refiner. Other mechanical refiners may be employed, and chemical refining aids may be introduced.

Mechanically treating (refining) may employ one or more known techniques such as, but by no means limited to, milling, grinding, beating, sonicating, or any other means to reduce cellulose particle size. Such refiners are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, *Handbook for Pulp & Paper Technologists*, Tappi Press, 1992.

A blow tank may be situated downstream of the mechanical refiner, so that the mechanical refiner operates under pressure. The pressure of the mechanical refiner may be the same as the digestor pressure, or it may be different. In some embodiments, the mechanical refiner is operated at a refining pressure selected from about 30 psig to about 300 psig, such as about 40, 50, 60, 70, 80, 90, 100, 110, 120, 130, 140, 150, 160, 170, 180, 190, 200, 210, 220, 230, 240, 250, 260, 270, 280, or 290 psig.

A blow tank may be situated upstream of the mechanical refiner, so that the mechanical refiner operates under reduced pressure or atmospheric pressure. In some embodiments, the mechanical refiner is operated a refining pressure of less than about 50, 45, 40, 35, 30, 25, 20, 15, 10, or 5 psig, or at or about atmospheric pressure (0 psig).

In certain embodiments of the invention, a first blow tank is situated upstream of the mechanical refiner and a second blow tank is situated downstream of the mechanical refiner. In this scenario, the pressure is reduced somewhat between the digestor and the refiner, which operates above atmospheric pressure. Following the refining, the pressure is released in the second blow tank. In some embodiments, the mechanical refiner is operated at a refining pressure selected from about 10 psig to about 150 psig, such as about 20 psig to about 100 psig, or about 25, 30, 35, 40, 45, 50, 55, 60, 65, 70, or 75 psig.

A pressurized refiner may operate at the same pressure as the digestor, or at a different pressure. In some embodiments, both the digestor and the refiner operate in a pressure range corresponding to equilibrium steam saturation temperatures from about 170° C. to about 210° C., such as about 180° C. to about 200° C. In some embodiments, a pressurized refiner is fed by a screw between the digestor and the refiner.

In principle, the pressure in the refiner could be higher than the digestor pressure, due to mechanical energy input. For example, a high-pressure screw feeder could be utilized to increase pressure, if desired, in refining. Also, it will be recognized that localized pressures (forces) may be higher than the vapor pressure, due to the presence of mechanical surface force (e.g., plates) impacting the solid material or slurry.

In some embodiments, the vapor is separated from a blow tank, and heat is recovered from at least some of the vapor. At least some of the vapor may be compressed and returned to the digestor. Some of the vapor may be purged from the process.

The enzymes introduced or present in the enzymatic hydrolysis unit may include cellulases and optionally hemicellulases. The enzymes may include endoglucanases and exoglucanases.

The process may further include removal of one or more fermentation inhibitors by stripping, conducted for example following step (e).

The process may further include a step of fermenting the fermentable sugars to a fermentation product; and concentrating and purifying the fermentation product. In various embodiments, the fermentation product may be selected from ethanol, n-butanol, 1,4-butanediol, succinic acid, lactic acid, or combinations thereof.

Some embodiments further include comprising removing a solid stream containing lignin following step (e) but prior to fermentation of the fermentable sugars. In these or other embodiments, the process may further include removing a solid stream containing lignin following fermentation of the fermentable sugars. The lignin may be combusted or use for other purposes.

Other variations of the invention provide a process for producing fermentable sugars from cellulosic biomass, the process comprising:
 (a) providing a feedstock comprising cellulosic biomass;
 (b) digesting the feedstock with a reaction solution including steam and/or hot water in a digestor under effective reaction conditions to produce a digested stream containing cellulose-rich solids, hemicellulose oligomers, and lignin;
 (c) conveying the digested stream through a mechanical refiner, thereby generating a refined stream with reduced average particle size of the cellulose-rich solids;
 (d) introducing enzymes to the mechanical refiner and maintaining effective hydrolysis conditions to produce sugars from the cellulose-rich solids and optionally from the hemicellulose oligomers, optionally simultaneously with step (c); and
 (e) recovering or further processing at least some of the sugars as fermentable sugars.

In some embodiments, the enzymes are introduced directly to the mechanical refiner. In these or other embodiments, the enzymes are introduced to the digested stream, upstream of the mechanical refiner. The enzymes may include cellulases (e.g., endoglucanases and exoglucanases) and hemicellulases.

The effective hydrolysis conditions may include a maximum temperature of 75° C. or less, preferably 65° C. or less, within the mechanical refiner. In some embodiments, the effective hydrolysis conditions include a hydrolysis temperature of about 30, 35, 40, 45, 50, 55, 60, 65, or 70° C. within the mechanical refiner. These are average temperatures within the refining zone. Local hot spots may be present within the refiner, such as in regions of high-shear contact between cellulose-rich solids and metal plates.

The reaction solution may comprise hot water or steam in saturated, superheated, or supersaturated form. In some embodiments, the reaction solution further comprises an acid, such as a sulfur-containing acid. In some embodiments, the reaction solution further comprises acetic acid, which may be (at least in part) acetic acid recovered from the digested stream.

The mechanical refiner may be selected from the group consisting of a hot-blow refiner, a hot-stock refiner, a blow-line refiner, a disk refiner, a conical refiner, a cylindrical refiner, an in-line defibrator, a homogenizer, and combinations thereof. In certain embodiments, the mechanical refiner is one or more blow-line refiners.

In some embodiments, a blow tank is situated upstream of the mechanical refiner. The mechanical refiner is preferably operated at or about atmospheric pressure, due to the presence of enzymes.

In some embodiments, vapor is separated from a blow tank, and heat is recovered from at least some of the vapor. Some or all of the vapor may be compressed and returned to the digestor. Some of the vapor may be purged from the process.

The process may also include removal of one or more fermentation inhibitors by stripping. The stripping may be conducted following step (e), prior to fermentation. One fermentation inhibitor is acetic acid, which may be recycled to the digestor, i.e. step (b).

The process may further include a step of fermenting the fermentable sugars to a fermentation product, such as ethanol, n-butanol, 1,4-butanediol, succinic acid, lactic acid, or combinations thereof. The fermentation product may be concentrated and purified.

The process may further include a solid stream containing lignin (i) following step (d) but prior to fermentation of the fermentable sugars and/or (ii) following fermentation of the fermentable sugars. The lignin may be recovered for various uses, such as combustion (energy).

In some embodiments, a blow tank is situated downstream of the mechanical refiner. In other embodiments, a blow tank is situated upstream of the mechanical refiner. In certain embodiments, a first blow tank is situated downstream of the mechanical refiner and a second blow tank is situated upstream of the mechanical refiner. The vapor separated in step (d) may be separated from a blow tank.

Note that "blow tank" should be broadly construed to include not only a tank but any other apparatus or equipment capable of allowing a pressure reduction in the process stream. Thus a blow tank may be a tank, vessel, section of pipe, valve, separation device, or other unit.

In some embodiments, following a digestor to remove hemicellulose, an intermediate blow is performed to, for example, about 40 psig. The material is sent to a blowline refiner, and then to a final blow to atmospheric pressure.

In some embodiments, a cold blow discharger is utilized to feed a pressurized refiner. In some embodiments, a transfer conveyor is utilized to feed a pressurized refiner.

The refining may be conducted at a wide range of solids concentrations (consistency), including from about 2% to about 50% consistency, such as about 4%, 6%, 8%, 10%, 15%, 20%, 30%, 35%, or 40% consistency.

In some embodiments, heat is recovered from at least some of the vapor, using the principles of heat integration. At least some of the vapor may be compressed and returned to the digestor. Some of the vapor may be purged from the process.

In some embodiments, enzymes introduced or present in the enzymatic hydrolysis unit may include not only cellulases but also hemicellulases. In certain embodiments, enzymes introduced or present in the enzymatic hydrolysis unit include endoglucanases and exoglucanases.

The reaction solution optionally includes an acid catalyst, to assist in extraction of hemicelluloses from the starting material, and possibly to catalyze some hydrolysis. In some embodiments, the acid is a sulfur-containing acid (e.g., sulfur dioxide). In some embodiments, the acid is acetic acid, which may be recovered from the digested stream (i.e., from downstream operations).

The starting feedstock may include sucrose, such as in the case of energy cane. A majority of the sucrose may be recovered as part of the fermentable sugars.

The process may include cleaning the starting feedstock, by wet or dry cleaning. The process may include size reduction, hot-water soaking, dewatering, steaming, or other operations, upstream of the digestor.

The process may further include removal of one or more fermentation inhibitors (such as acetic acid or furfural) by stripping. This stripping may be conducted following step (e), i.e. treating the hydrolyzed cellulose stream, prior to fermentation. Alternatively, or additionally, the stripping may be conducted on a stream following digestion, such as in the blow line, or as part of an acetic acid recycle system.

The process may further include a step of fermenting the fermentable sugars to a fermentation product. Typically the process will further include concentration and purification of the fermentation product. The fermentation product may be selected from ethanol, n-butanol, 1,4-butanediol, succinic acid, lactic acid, or combinations thereof, for example. The lignin may be combusted for energy production, for example.

Some variations provide a process for producing fermentable sugars from cellulosic biomass, the process comprising:
  (a) providing a feedstock comprising cellulosic biomass;
  (b) digesting the feedstock with a reaction solution including steam and/or hot water in a digestor under effective reaction conditions to produce a digested stream containing cellulose-rich solids, hemicellulose oligomers, and lignin;
  (c) conveying the digested stream through a mechanical refiner, thereby generating a refined stream with reduced average particle size of the cellulose-rich solids;
  (d) separating a vapor from the refined stream;
  (e) introducing the refined stream to an acid hydrolysis unit under effective hydrolysis conditions to produce sugars from the cellulose-rich solids and optionally from the hemicellulose oligomers;
  (f) recovering or further processing at least some of the sugars as fermentable sugars.

Certain embodiments provide a process for producing ethanol from cellulosic biomass, the process comprising:
  (a) providing a feedstock comprising cellulosic biomass;
  (b) digesting the feedstock with a reaction solution including steam and/or hot water in a digestor under effective reaction conditions to produce a digested stream containing cellulose-rich solids, hemicellulose oligomers, and lignin;
  (c) conveying the digested stream through a blow-line refiner, thereby generating a refined stream with reduced average particle size of the cellulose-rich solids;
  (d) separating a vapor from the refined stream;
  (e) introducing the refined stream to an enzymatic hydrolysis unit under effective hydrolysis conditions to produce sugars from the cellulose-rich solids and from the hemicellulose oligomers;
  (f) fermenting the sugars to produce ethanol in dilute solution; and
  (g) concentrating the dilute solution to produce an ethanol product.

In some embodiments, the extraction solution comprises steam in saturated, superheated, or supersaturated form. In some embodiments, the extraction solution comprises hot water. Additives may be present, such as acid or base catalysts, or other compounds present in recycled streams. The fraction of starting hemicellulose that is extracted into solution may be from about 60% to about 95%, such as about 75%, 80%, 85%, or 90%.

In some embodiments, the process includes washing the cellulose-rich solids using an aqueous wash solution, to produce a wash filtrate; and optionally combining at least some of the wash filtrate with the extract liquor. In some of these embodiments, the process further includes pressing the cellulose-rich solids to produce the washed cellulose-rich solids and a press filtrate; and optionally combining at least some of the press filtrate with the extract liquor.

The process may include countercurrent washing, such as in two, three, four, or more washing stages. The separation/washing may be combined with the application of enzymes, in various ways.

In some embodiments, a refiner is configured to cause at least some liquefaction as a result of enzymatic action on the cellulose-rich solids. "Liquefaction" means partial hydrolysis of cellulose to form glucose oligomers (i.e. glucan) that dissolve into solution, but not total hydrolysis of cellulose to glucose monomers (saccharification). Various fractions of cellulose may be hydrolyzed during liquefaction. In some embodiments, the fraction of cellulose hydrolyzed may be from about 5% to about 90%, such as about 10% to about 75% (e.g. about 15%, 20%, 25%, 30%, 35%, 40%, 45%, 50%, 55%, 60%, 65%, or 70%). In certain embodiments, there is no separate liquefaction tank or reactor; liquefaction and hydrolysis occur in the same vessel (e.g., refiner or hydrolysis reactor).

A "liquefaction-focused blend of enzymes" means a mixture of enzymes that includes at least one enzyme capable of hydrolyzing cellulose to form soluble oligomers. In some embodiments, a liquefaction-focused blend of enzymes includes both endoglucanases and exoglucanases. Endoglucanases are cellulases that attack low-crystallinity regions in the cellulose fibers by endoaction, creating free chain-ends. Exoglucanases or cellobiohydrolases are cellulases that hydrolyze the 1,4-glycocidyl linkages in cellobiose.

Various cellulase enzymes may be utilized in the liquefaction-focused blend of enzymes, such as one or more enzymes recited in Verardi et al., "Hydrolysis of Lignocellulosic Biomass: Current Status of Processes and Technologies and Future Perspectives," *Bioethanol*, Prof. Marco Aurelio Pinheiro Lima (Ed.), ISBN: 978-953-51-0008-9, InTech (2012), which is hereby incorporated by reference.

Some embodiments employ thermotolerant enzymes obtained from thermophilic microrganisms. The thermophilic microrganisms can be grouped in thermophiles (growth up to 60° C.), extreme thermophiles (65-80° C.) and hyperthermophiles (85-110° C.). The unique stability of the enzymes produced by these microrganisms at elevated temperatures, extreme pH and high pressure (up to 1000 bar) makes them valuable for processes at harsh conditions. Also, thermophilic enzymes have an increased resistance to many denaturing conditions such as the use of detergents which can be an efficient means to obviate the irreversible adsorption of cellulases on the substrates. Furthermore, the utilization of high operation temperatures, which cause a decrease in viscosity and an increase in the diffusion coefficients of substrates, have a significant influence on the cellulose solubilization. It is worth noting that most thermophilic cellulases do not show inhibition at high level of reaction products (e.g. cellobiose and glucose). As consequence, higher reaction rates and higher process yields are expected. The high process temperature also reduces contamination. See Table 6, "Thermostable cellulases" in Verardi et al., cited previously, for exemplary thermotolerant enzymes that may be used in the liquefaction-focused blend of enzymes.

In some embodiments, an enzyme is selected such that at a high temperature, the enzyme is able to catalyze liquefaction (partial hydrolysis) but not saccharification (total hydrolysis). When the temperature is reduced, the same enzyme is able to catalyze saccharification to produce glucose.

When the hydrolysis process employs enzymes, these enzymes will typically contain cellulases and hemicellulases. The cellulases here may include β-glucosidases that convert cellooligosaccharides and disaccharide cellobiose into glucose. There are a number of enzymes that can attack hemicelluloses, such as glucoronide, acetylesterase, xylanase, β-xylosidase, galactomannase and glucomannase. Exemplary acid catalysts include sulfuric acid, sulfur dioxide, hydrochloric acid, phosphoric acid, and nitric acid.

In some embodiments, non-acid and non-enzyme catalysts may be employed for co-hydrolyzing the glucose oligomers and the hemicellulose oligomers. For example, base catalysts, solid catalysts, ionic liquids, or other effective materials may be employed.

The process further comprises a step of fermenting the fermentable sugars to a fermentation product (such as ethanol), in some embodiments.

Other variations provide a process for producing fermentable sugars from cellulosic biomass, the process comprising:
(a) providing a feedstock comprising cellulosic biomass;
(b) extracting the feedstock with steam and/or hot water under effective extraction conditions to produce an extract liquor containing hemicellulose oligomers, dissolved lignin, and cellulose-rich solids;
(c) separating at least a portion of the cellulose-rich solids from the extract liquor, to produce washed cellulose-rich solids;
(d) removing a portion of glucan contained in the washed cellulose-rich solids by contacting the washed cellulose-rich solids with a liquefaction-focused blend of enzymes, to release glucose oligomers;
(e) hydrolyzing the glucose oligomers with a first hydrolysis catalyst, to produce glucose;
(f) hydrolyzing the hemicellulose oligomers with a second hydrolysis catalyst, to produce hemicellulose monomers; and
(g) recovering the glucose and hemicellulose monomers, individually or in combination, as fermentable sugars.

In some embodiments, the first hydrolysis catalyst includes cellulases. In some embodiments, the second hydrolysis catalyst includes hemicellulases. In other embodiments, the first hydrolysis catalyst and the second hydrolysis catalyst are acid catalysts, base catalysts, ionic liquids, solid catalysts, or other effective materials. The first hydrolysis catalyst may be the same as, or different than, the second hydrolysis catalyst.

In some embodiments, the glucose is recovered in a separate stream from the hemicellulose monomers. In other embodiments, the glucose and the hemicellulose monomers are recovered in the same stream. The process may include fermentation of the glucose and/or the fermentable hemicellulose sugars to a fermentation product.

The biomass feedstock may be selected from hardwoods, softwoods, forest residues, agricultural residues (such as sugarcane bagasse), industrial wastes, consumer wastes, or combinations thereof. In any of these processes, the feedstock may include sucrose. In some embodiments with sucrose present in the feedstock, a majority of the sucrose is recovered as part of the fermentable sugars. In order to preserve sucrose (when present), it is preferred to utilize enzymes rather than acid catalysts for cellulose hydrolysis.

In some embodiments, the process starts as biomass is received or reduced to approximately ¼" thickness. In a first step of the process, the biomass is fed (e.g., from a bin) to a pressurized extraction vessel operating continuously or in batch mode. The biomass may first be steamed or water-washed to remove dirt and entrained air. The biomass may be immersed with aqueous liquor or saturated vapor and heated to a temperature between about 100° C. to about 250° C., for example 150° C., 160° C., 170° C., 180° C., 190° C., 200° C., or 210° C. Preferably, the biomass is heated to about 180° C. to 210° C.

The pressure in the pressurized vessel may be adjusted to maintain the aqueous liquor as a liquid, a vapor, or a combination thereof. Exemplary pressures are about 1 atm to about 30 atm, such as about 3 atm, 5 atm, 10 atm, or 15 atm.

The solid-phase residence time for the digestor (pressurized extraction vessel) may vary from about 2 minutes to about 4 hours, such as about 5 minutes to about 1 hour. In certain embodiments, the digestor residence time is controlled to be about 5 to 15 minutes, such as 5, 6, 7, 8, 9, 10, 11, 12, 13, 14 or 15 minutes. The liquid-phase residence time for the digestor may vary from about 2 minutes to about 4 hours, such as about 5 minutes to about 1 hour. The vapor-phase residence time for the digestor may vary from about 1 minute to about 2 hours, for example, such as about 3 minutes to about 30 minutes. The solid-phase, liquid-phase, and vapor-phase residence times may all be about the same, or they may be independently controlled according to reactor-engineering principles (e.g., recycling and internal recirculation strategies).

The aqueous liquor may contain acidifying compounds, such as (but not limited to) sulfuric acid, sulfurous acid, sulfur dioxide, acetic acid, formic acid, or oxalic acid, or combinations thereof. The dilute acid concentration can range from 0.01% to 10% as necessary to improve solubility of particular minerals, such as potassium, sodium, or silica. Preferably, the acid concentration is selected from about 0.01% to 4%, such as 0.1%, 0.5%, 1%, 1.5%, 2%, 2.5%, 3%, or 3.5%.

A second step may include depressurization of the extracted chips into a blow tank or other tank or unit. The vapor can be used for heating the incoming woodchips or cooking liquor, directly or indirectly. The volatilized organic acids (e.g., acetic acid), which are generated or included in the cooking step, may be recycled back to the cooking.

A third step may include mechanically refining the extracted chips. This step (using, for example, a blow-line refiner) may be done before or after depressurization. Optionally, refined solids may be washed. The washing may be accomplished with water, recycled condensates, recycled permeate, or combination thereof. Washing typically removes most of the dissolved material, including hemicelluloses and minerals. The final consistency of the dewatered cellulose-rich solids may be increased to 30% or more, preferably to 50% or more, using a mechanical pressing device. The mechanical pressing device may be integrated with the mechanical refiner, to accomplish combined refining and washing.

A fourth step may include hydrolyzing the extracted chips with enzymes to convert some of the cellulose to glucose. When enzymes are employed for the cellulose hydrolysis, the enzymes preferably include cellulase enzymes. Enzymes may be introduced to the extracted chips along with water, recycled condensates, recycled permeate, additives to adjust pH, additives to enhance hydrolysis (such as lignosulfonates), or combinations thereof.

Some or all of the enzymes may be added to the blow line before or at the blow-line refiner, for example, to assist in enzyme contact with fibers. In some embodiments, at least a portion of enzymes are recycled in a batch or continuous process.

When an acid is employed for the cellulose hydrolysis, the acid may be selected from sulfuric acid, sulfurous acid, sulfur dioxide, formic acid, acetic acid, oxalic acid, or combinations thereof. Acids may be added to the extracted chips before or after mechanical refining. In some embodiments, dilute acidic conditions are used at temperatures between about 100° C. and 190° C., for example about 120° C., 130° C., 140° C., 150° C., 160° C., or 170° C., and preferably from 120° C. to 150° C. In some embodiments, at least a portion of the acid is recycled in a batch or continuous process.

The acid may be selected from sulfuric acid, sulfurous acid, or sulfur dioxide. Alternatively, or additionally, the acid may include formic acid, acetic acid, or oxalic acid from the cooking liquor or recycled from previous hydrolysis.

A fifth step may include conditioning of hydrolysate to remove some or most of the volatile acids and other fermentation inhibitors. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) to assist in the removal of hemicelluloses or minerals from the biomass. This recycle of organic acids, such as acetic acid, may be optimized along with process conditions that may vary depending on the amount recycled, to improve the cooking effectiveness.

A sixth step may include recovering fermentable sugars, which may be stored, transported, or processed. A sixth step may include fermenting the fermentable sugars to a product, as further discussed below.

A seventh step may include preparing the solid residuals (containing lignin) for combustion. This step may include refining, milling, fluidizing, compacting, and/or pelletizing the dried, extracted biomass. The solid residuals may be fed to a boiler in the form of fine powder, loose fiber, pellets, briquettes, extrudates, or any other suitable form. Using known equipment, solid residuals may be extruded through a pressurized chamber to form uniformly sized pellets or briquettes.

Some embodiments of the invention enable processing of "agricultural residues," which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof. In certain embodiments, the agricultural residue is sugarcane bagasse.

In some embodiments, the fermentable sugars are recovered from solution, in purified form. In some embodiments, the fermentable sugars are fermented to produce of biochemicals or biofuels such as (but by no means limited to) ethanol, 1-butanol, isobutanol, acetic acid, lactic acid, or any other fermentation products. A purified fermentation product may be produced by distilling the fermentation product, which will also generate a distillation bottoms stream containing residual solids. A bottoms evaporation stage may be used, to produce residual solids.

Following fermentation, residual solids (such as distillation bottoms) may be recovered, or burned in solid or slurry form, or recycled to be combined into the biomass pellets. Use of the fermentation residual solids may require further removal of minerals. Generally, any leftover solids may be used for burning, after concentration of the distillation bottoms.

Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

In certain embodiments, the process further comprises combining, at a pH of about 4.8 to 10 or higher, a portion of vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate.

In some variations, the invention provides a process for separating fermentation inhibitors from a biomass-derived hydrolysate, the process comprising:
  (a) providing a biomass-derived liquid hydrolysate stream comprising a fermentation inhibitor;
  (b) introducing the liquid hydrolysate stream to a stripping column;
  (c) introducing a steam-rich vapor stream to the stripping column to strip at least a portion of the fermentation inhibitor from the liquid hydrolysate stream;
  (d) recovering, from the stripping column, a stripped liquid stream and a stripper vapor output stream, wherein the stripped liquid stream has lower fermentation inhibitor concentration than the liquid hydrolysate stream;
  (e) compressing the stripper vapor output stream to generate a compressed vapor stream;
  (f) introducing the compressed vapor stream, and a water-rich liquid stream, to an evaporator;
  (g) recovering, from the evaporator, an evaporated liquid stream and an evaporator output vapor stream; and
  (h) recycling at least a portion of the evaporator output vapor stream to the stripping column as the steam-rich vapor stream, or a portion thereof.

The biomass-derived hydrolysate may be the product of acidic or enzymatic hydrolysis, or it may be the extracted solution from the digestor, for example. In some embodiments, the fermentation inhibitor is selected from the group consisting of acetic acid, formic acid, formaldehyde, acetaldehyde, lactic acid, furfural, 5-hydroxymethylfurfural, furans, uronic acids, phenolic compounds, sulfur-containing compounds, and combinations or derivatives thereof.

In certain embodiments, the fermentation inhibitor is acetic acid. The stripped liquid stream preferably has less than 10 g/L acetic acid concentration, such as less than 5 g/L acetic acid concentration.

In some embodiments, the water-rich liquid stream contains biomass solids that are concentrated in the evaporator. These biomass solids may be derived from the same biomass feedstock as is the biomass-derived liquid hydrolysate, in an integrated process.

Optionally, the fermentation inhibitor is recycled to a previous unit operation (e.g., digestor or reactor) for generating the biomass-derived liquid hydrolysate stream, to assist with hydrolysis or pretreatment of a biomass feedstock or component thereof. For example, acetic acid may be recycled for this purpose, to aid in removal of hemicelluloses from biomass and/or in oligomer hydrolysis to monomer sugars.

Some variations provide a process for separating fermentation inhibitors from a biomass-derived hydrolysate, the process comprising:
- (a) providing a biomass-derived liquid hydrolysate stream comprising a fermentation inhibitor;
- (b) introducing the liquid hydrolysate stream to a stripping column;
- (c) introducing a steam-rich vapor stream to the stripping column to strip at least a portion of the fermentation inhibitor from the liquid hydrolysate stream;
- (d) recovering, from the stripping column, a stripped liquid stream and a stripper vapor output stream, wherein the stripped liquid stream has lower fermentation inhibitor concentration than the liquid hydrolysate stream;
- (e) introducing the stripper vapor output stream, and a water-rich liquid stream, to an evaporator;
- (f) recovering, from the evaporator, an evaporated liquid stream and an evaporator output vapor stream;
- (g) compressing the evaporator output vapor stream to generate a compressed vapor stream; and
- (h) recycling at least a portion of the compressed vapor stream to the stripping column as the steam-rich vapor stream, or a portion thereof.

In some embodiments, the evaporator is a boiler, the water-rich liquid stream comprises boiler feed water, and the evaporated liquid stream comprises boiler condensate.

The process may be continuous, semi-continuous, or batch. When continuous or semi-continuous, the stripping column may be operated countercurrently, cocurrently, or a combination thereof.

In certain variations of the present invention, a process for separating and recovering a fermentation inhibitor from a biomass-derived hydrolysate comprises:
- (a) providing a biomass-derived liquid hydrolysate stream comprising a fermentation inhibitor;
- (b) introducing the liquid hydrolysate stream to a stripping column;
- (c) introducing a steam-rich vapor stream to the stripping column to strip at least a portion of the fermentation inhibitor from the liquid hydrolysate stream;
- (d) recovering, from the stripping column, a stripped liquid stream and a stripper vapor output stream, wherein the stripped liquid stream has lower fermentation inhibitor concentration than the liquid hydrolysate stream;
- (e) introducing the stripper vapor output stream, and a water-rich liquid stream, to a rectification column;
- (f) recovering, from the rectification column, a rectified liquid stream and a rectification column vapor stream, wherein the rectified liquid stream has higher fermentation inhibitor concentration than the liquid hydrolysate stream; and
- (g) recycling at least a portion of the rectification column vapor stream to the stripping column as the steam-rich vapor stream, or a portion thereof.

The fermentation inhibitor may be selected from the group consisting of acetic acid, formic acid, formaldehyde, acetaldehyde, lactic acid, furfural, 5-hydroxymethylfurfural, furans, uronic acids, phenolic compounds, sulfur-containing compounds, and combinations or derivatives thereof. In some embodiments, the fermentation inhibitor comprises or consists essentially of acetic acid.

In the case of acetic acid, the stripped liquid stream preferably has less than 10 g/L acetic acid concentration, such as less than 5 g/L acetic acid concentration. The rectification column vapor stream preferably has less than 0.5 g/L acetic acid concentration, such as less than 0.1 g/L acetic acid concentration. The rectified liquid stream preferably has at least 25 g/L acetic acid concentration, such as about 40 g/L or more acetic acid. In some embodiments, the rectified liquid stream has at least 10 times higher concentration of acetic acid compared to the stripped liquid stream. In certain embodiments, the process further comprises recovering the acetic acid contained in the rectified liquid stream using liquid-vapor extraction or liquid-liquid extraction.

In some embodiments, the water-rich liquid stream includes evaporator condensate. The evaporator condensate may be derived from an evaporator in which biomass solids are concentrated, and the biomass solids may be derived from the same biomass feedstock as the biomass-derived liquid hydrolysate, in an integrated process.

Optionally, the fermentation inhibitor (e.g., acetic acid) is recycled to a previous unit operation for generating the biomass-derived liquid hydrolysate stream, to assist with hydrolysis or pretreatment of a biomass feedstock or component thereof.

The process may be continuous, semi-continuous, or batch. When continuous or semi-continuous, the stripping column may be operated countercurrently, cocurrently, or a combination thereof. The rectification column may be operated continuous, semi-continuous, or batch.

In various embodiments, step (g) comprises compressing and/or conveying the rectification column vapor stream using a device selected from the group consisting of a mechanical centrifugal vapor compressor, a mechanical axial vapor compressor, a thermocompressor, an ejector, a diffusion pump, a turbomolecular pump, and combinations thereof.

If desired, a base or other additive may be included in the water-rich liquid stream, or separately introduced to the rectification column, to produce salts or other reaction products derived from fermentation inhibitors. In some embodiments, the water-rich liquid stream includes one or more additives capable of reacting with the fermentation inhibitor. In certain embodiments, the fermentation inhibitor includes acetic acid, and the one or more additives include a base. An acetate salt may then be generated within the rectification column, or in a unit coupled to the rectification column. Optionally, the acetate salt may be separated and recovered using liquid-vapor extraction or liquid-liquid extraction.

This patent application hereby incorporates by reference herein the following commonly owned patents: "PROCESS FOR OBTAINING BIOCHEMICALS IN A ZERO LIQUID DISCHARGE PLANT," U.S. Pat. No. 8,211,680; "PROCESS FOR PRODUCING HEMICELLULOSE SUGARS AND ENERGY FROM BIOMASS," U.S. Pat. No. 8,518,672; "PROCESS FOR PRODUCING ALCOHOL AND OTHER BIOPRODUCTS FROM BIOMASS EXTRACTS IN A KRAFT PULP MILL," U.S. Pat. No. 8,518,213; "DEICER COMPOSITIONS AND PROCESSES FOR MAKING DEICERS," U.S. Pat. No. 8,679,364; "CORROSION-INHIBITING DEICERS DERIVED FROM BIOMASS," U.S. Pat. No. 8,845,923; "PROCESSES FOR PRODUCING FERMENTABLE SUGARS AND LOW-ASH BIOMASS FOR COMBUSTION OR PELLETS," U.S. Pat. No. 8,685,685; "PROCESS FOR OBTAINING BIOCHEMICALS IN A ZERO LIQUID DISCHARGE PLANT," U.S. Pat. No. 8,785,155; "PROCESSES FOR PRODUCING FERMENTABLE SUGARS AND ENERGY-DENSE BIOMASS FOR COMBUSTION," U.S. Pat. No. 8,906,657; "STEPWISE ENZYMATIC HYDROLYSIS PROCESS FOR CONVERTING CELLULOSE TO GLUCOSE," U.S. Pat. No. 9,139,857; and "PROCESSES FOR PRODUCING CELLULOSE PULP, SUGARS, AND CO-PRODUCTS FROM LIGNOCELLULOSIC BIOMASS," U.S. Pat. No. 9,347,176.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method of enzymatically hydrolyzing pretreated lignocellulosic biomass at high solids concentration, said method comprising: (a) providing pretreated lignocellulosic biomass containing cellulose; (b) introducing said pretreated lignocellulosic biomass to an enzymatic hydrolysis reactor under effective hydrolysis conditions and in the presence of enzymes including cellulases, to enzymatically hydrolyze said cellulose to glucose monomer and glucose oligomers, wherein said pretreated lignocellulosic biomass is present in said enzymatic hydrolysis reactor at a solids concentration of at least 20 wt %; and (c) circulating a liquid stream in a circulation line configured from an output of said enzymatic hydrolysis reactor back to an input of said enzymatic hydrolysis reactor, wherein said glucose monomer is removed from said circulation line, wherein said method further comprises a glucose oligomer hydrolysis step to generate a second amount of glucose monomer from said glucose oligomers, wherein said glucose oligomer hydrolysis step is integrated with step (c), and wherein said method further comprises introducing an external lignin-containing surfactant to said enzymatic hydrolysis reactor during step (b) or step (c), wherein said solids concentration is at least 25 wt %.

2. The method of claim 1, wherein said glucose oligomers are also removed from said circulation line.

3. The method of claim 1, wherein an additional quantity of cellulase enzymes is introduced to said circulation line, to convert said glucose oligomers to said second amount of glucose monomer.

4. The method of claim 1, wherein said solids concentration is at least 30 wt %.

* * * * *